US007807362B2

(12) United States Patent
Kim et al.

(10) Patent No.: US 7,807,362 B2
(45) Date of Patent: Oct. 5, 2010

(54) DIAGNOSIS OF ATTENTION DEFICIT HYPERACTIVITY DISORDER

(75) Inventors: Kwang-Soo Kim, Lexington, MA (US); Chun-Hyung Kim, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 660 days.

(21) Appl. No.: 11/674,817

(22) Filed: Feb. 14, 2007

(65) Prior Publication Data

US 2009/0253617 A1    Oct. 8, 2009

Related U.S. Application Data

(60) Provisional application No. 60/773,459, filed on Feb. 15, 2006.

(51) Int. Cl.
*C12Q 1/68*    (2006.01)
*C12Q 1/00*    (2006.01)
*G01N 33/566*    (2006.01)
*G01N 33/567*    (2006.01)

(52) U.S. Cl. ............................... 435/6; 435/4; 436/501; 436/503; 436/504

(58) Field of Classification Search ........................ None
See application file for complete search history.

(56) References Cited

U.S. PATENT DOCUMENTS

2003/0170875 A1    9/2003    Robertson et al.

OTHER PUBLICATIONS

Barr et al., The Norepinephrine Transporter Gene and Attention-Deficit Hyperactivity Disorder, Am. J. Med. Genet., 114:255-259 (2002).
Bhaduri et al., Analysis of Polymorphisms in the Dopamine Beta Hydroxylase Gene: Association with Attention Deficit Hyperactivity Disorder in Indian Children, Indian Pediatrics, 42:123-129 (2005).
Bobb et al., Support for Association Between ADHD and Two Candidate Genes: *NET1* and *DRD1*, Am. J. Med. Genet., 134B:67-72 (2005).
Brookes et al., DNA Pooling Analysis of ADHD and Genes Regulating Vesicle Release of Neurotransmitters, Am. J. Med. Genet., 139B:33-37 (2005).
DeLuca et al., No Evidence of Linkage or Association Between the Norepinephrine Transporter (NET) Gene *MnlI* Polymorphism and Adult ADHD, Am. J. Med. Genet., 124B:38-40 (2004).
Eisenberg et al., A Haplotype Relative Risk Study of the Dopamine D4 Receptor (DRD4) Exon III Repeat Polymorphism and Attention Deficit Hyperactivity Disorder (ADHD), Am. J. Med. Genet., 96:258-261 (2000).
Funahashi et al., δ-crystallin enhancer binding protein δEF1 is a zinc finger-homeodomain protein implicated in postgastrulation embryogenesis, *Development*, 119:433-446 (1993).
Hahn et al., A Mutation in the Human Norepinephrine Transporter Gene (SLC6A2) Associated with Orthostatic Intolerance Disrupts Surface Expression of Mutant and Wild-Type Transporters, *J Neurosci* 23:4470-4478 (2003).
Hahn et al., Single Nucleotide Polymorphisms in the Human Norepinephrine Transporter Gene Affect Expression, Trafficking, Antidepressant Interaction, and Protein Kinase C Regulation, *Mol Pharmacol* 68:457-466 (2005).
Heim, Christine and Nemeroff, Charles B., The Role of Childhood Trauma in the Neurobiology of Mood and Anxiety Disorders: Preclinical and Clinical Studies, *Biol Psychiatry*, 49:1023-1039 (2001).
Heinemeyer et al., Databases on transcriptional regulation: TRANSFAC, TRRD and COMPEL, Nucleic Acids Research, 26(1):362-367 (1998).
Iversen, L., Neurotransmitter transporters: fruitful targets for CNS drug discovery, Mol. Psychiatry, 5:357-362 (2000).
Kang, Yibin and Massague, Joan, Epithelial-Mesenchymal Transitions: Twist in Development and Metastasis, *Cell*, 118:277-279 (2004).
Kim et al., A polymorphism in the norepinephrine transorter gene alters promoter activity and is associated with attention-deficit hyperactivity disorder, Proc. Natl. Acad. Sci. (USA), 103:19164-19169 (2006).
Klimek et al., Reduced Levels of Norepinephrine Transporters in the Locus Coeruleus in Major Depression, *J Neurosci* 17:8451-8458 (1997).
Marin, Faustino and Nieto, M. Angela, The Expression of *Scratch* Genes in the Developing and Adult Brain, *Dev. Dyn.* 235:2586-2591 (2006).
Nakakura et al., Mammalian Scratch: A neural-specific Snail family transcriptional repressor, Proc. Natl. Acad. Sci. USA 98:4010-4015, (2001).
Nieto, M. Angela, The Snail Superfamily of Zinc-Finger Transcription Factors, *Nat Rev Mol Cell Biol*, 3:155-166 (2002).
Savagner et al., The Zinc-Finger Protein Slug Causes Desmosome Dissociation, an Initial and Necessary Step for Growth Factor-induced Epithelial-Mesenchymal Transition, J. Cell. Biol. 137:1403-1409, (1997).
Shannon et al., Orthostatic Intolerance and Tachycardia Associated with Norepinephrine-Transporter Deficiency, *N Engl J Med* 342, 541-9 (2000).
Solanto, M. V., Neuropsychopharmacological mechanisms of stimulant drug action in attention-deficit hyperactivity disorder: a review and integration, *Behav Brain Res*, 94:127-152 (1998).
Urwin et al., Anorexia nervosa (restrictive subtype) is associated with a polymorphism in the novel norephinephrine transporter gene promoter polymorphic region, *Mol Psychiatry* 7:652-657 (2002).
Xu et al., DNA Pooling Analysis of 21 Norepinephrine Transporter Gene SNPs With Attention Deficit Hyperactivity Disorder: No Evidence for Association, Am. J. Med. Genet., 134B:115-118 (2005).

(Continued)

*Primary Examiner*—Olga N Chernyshev
(74) *Attorney, Agent, or Firm*—Foley & Lardner LLP

(57) ABSTRACT

This invention features methods and compositions useful for the treatment and diagnosis of attentional disorders including attention deficit hyperactivity disorder (ADHD). Also disclosed are methods for identifying compounds useful for such therapy.

8 Claims, 10 Drawing Sheets

OTHER PUBLICATIONS

Yang et al., Association of Norepinephrine Transporter Gene With Methylphenidate Response, J Am Acad Child Adolesc Psychiatry, 43:1154-1158, (2004).

Kim et al., A Previously undescribed intron and extensive 5' upstream sequence, but not Phox2a-mediated transactivation, are necessary for high level cell type-specific expression of the human norepinephrine transporter gene. Journal of Biological Chemistry, 274 (10), p. 6507-6518, 1999.

Kim et al., A Proximal promoter domain containing a homeodomain-binding core motif interacts with multiple transcription factors, including HoxA5 and Phox2 proteins, and critically regulates cell type-specific transcription of the human norepinephrine transporter gene. Journal of Neuroscience, 22(7): 2579-2589, 2002.

Kopal et al., Mutation screening of the human norepineprine transporter promoter. American Journal of Medical Genetics Abstracts, 122B(1): 119, 2003.

Huezo-Diaz et al., Novel mutation identification of the human norepineprine transporter promoter. American Journal of Medical Genetics Abstracts, 138B(1): 86-87, 2005.

Urwin et al., Anorexia nervosa (restrictive subtype) is associated with a polymorphism in the novel norepinephrine transporter gene promoter polymorphic region. Molecular Psychiatry, 7:652-657, 2002.

International Search Report for PCT Patent Application No. PCT/US2007/004113.

A

-3072  ACCCCTTTGAACCACGAGTC  -309
       TGGGGAAACT GGTGCTCAG
              30          40

B
       ACCCCTTTGTTCCACGAGTC
       TGGGGAAACA GGTGCTCAG
              30          40

|         | 1 | 2 | 3 | 4 | 5 | 6 | 7 | 8 |
|---------|---|---|---|---|---|---|---|---|
| T probe | − | + | − | + | − | + | − | + |
| A probe | + | − | + | − | + | − | + | − |
| IVT-δEF1| + | + | − | − | − | − | − | − |
| IVT-Snail| − | − | + | + | − | − | − | − |
| IVT-Slug| − | − | − | − | + | + | − | − |
| IVT-Scrt| − | − | − | − | − | − | + | + |

FIGURE 5A

FIGURE 7A (SEQ ID NO.:1)

```
GAATTCAGGG CAGGTCAGCT GCAGTGTAAT ATATGCCTAT TGTCCCCTGA TCAAGACAGA -3975  (60)
AAGACAGAAT GAAAAGGAAG AAGGAAGGAA GGAACGGAGG AAAGAAAAGA GGGATGGAGG -3915  (120)
AAACAAATAT GTAGGCAAAC CTCTCCTCCT TTTTTTCCTT AGTCTCCTCA TTGGTGCCAT -3855  (180)
GGAGGTGTAG GTTCTGATAG CGTCCTCAGC GGACACAGGC CCTTGGATTC TAAATGTGTC -3795  (240)
CCAGCCCAGC TGTTGTGTGT CAGGGCCCCA GTGTCTGTGG GGAGATGGCC AGAGATGGAC -3735  (300)
TCACAGCATC AGCCATTGCC TTTTACCCCA TGGCCTGTGT CACCAAGTGC CATGGTAAGT -3675  (360)
GGAAGTGATG GCTCCCCAGA GATCACATTA GCTCTGATAA TGCTCCAGCC TCCCATGCAC -3615  (420)
AACTTGCCCT CAGGCCACCT GGCTGGGCAG GAAGAAGGGC TCCCAGAGAA GCCACATGGC -3555  (480)
CCCATGGCGG TGAGTCTGGG CGAGAGATGG AGAGAGACGC CTTCCCTTTT AGCCCAGTCC -3495  (540)
CAGCCTAGTG TCCTCACTGC TGACCCCCGG TAGTCTCTGA AACCACAGAT GGAGCTCCCA -3435  (600)
GACTTGCTGA TTGGCCCCCG TGATGGCGTG CGCATTAGGA GGAAATGCCT CCCTCCACCC -3375  (660)
TTGTAGCAAA CACTTCCAGC TCCATGCCCA CACCCCTTAT CATCCACTGT TCCTGCCAGT -3315  (720)
GCAGACCCAA CCCAATGGCT TCGTGCTGCC AGTACCTGGG GCTCTGCTGT TAGCCTTTCT -3255  (780)
CTGGCAGCAG GACAGGCTCA TCCCTCTTAT CAGACAGGCT GGACTTGGTG GAAGTTGAC  -3195  (840)
ACTCTGGGGG CGGCCTTCAT GGATAAATAC TGTAGTTTTC TTGCCCCTCA AGTGAGACAA -3135  (900)
CCCCAAGGCG TGCTCTGTGC AGTCTCCCGA GGCCCCACC AGGGCTGAGC ACCAGTTTCC  -3075  (960)
CCAGCAGCAA GTGCTCCTTA ATCTACTTTC TCCTGGTTTC CTTCCCTTTG CTGTCTC    -3018  (1020)
```

FIGURE 7B (SEQ ID NO.:2)

```
GAATTCAGGG CAGGTCAGCT GCAGTGTAAT ATATGCCTAT TGTCCCCTGA TCAAGACAGA -3975  (60)
AAGACAGAAT GAAAAGGAAG AAGGAAGGAA GGAACGGAGG AAAGAAAAGA GGGATGGAGG -3915  (120)
AAACAAATAT GTAGGCAAAC CTCTCCTCCT TTTTTTCCTT AGTCTCCTCA TTGGTGCCAT -3855  (180)
GGAGGTGTAG GTTCTGATAG CGTCCTCAGC GGACACAGGC CCTTGGATTC TAAATGTGTC -3795  (240)
CCAGCCCAGC TGTTGTGTGT CAGGGCCCCA GTGTCTGTGG GGAGATGGCC AGAGATGGAC -3735  (300)
TCACAGCATC AGCCATTGCC TTTTACCCCA TGGCCTGTGT CACCAAGTGC CATGGTAAGT -3675  (360)
GGAAGTGATG GCTCCCCAGA GATCACATTA GCTCTGATAA TGCTCCAGCC TCCCATGCAC -3615  (420)
AACTTGCCCT CAGGCCACCT GGCTGGGCAG GAAGAAGGGC TCCCAGAGAA GCCACATGGC -3555  (480)
CCCATGGCGG TGAGTCTGGG CGAGAGATGG AGAGAGACGC CTTCCCTTTT AGCCCAGTCC -3495  (540)
CAGCCTAGTG TCCTCACTGC TGACCCCCGG TAGTCTCTGA AACCACAGAT GGAGCTCCCA -3435  (600)
GACTTGCTGA TTGGCCCCCG TGATGGCGTG CGCATTAGGA GGAAATGCCT CCCTCCACCC -3375  (660)
TTGTAGCAAA CACTTCCAGC TCCATGCCCA CACCCCTTAT CATCCACTGT TCCTGCCAGT -3315  (720)
GCAGACCCAA CCCAATGGCT TCGTGCTGCC AGTACCTGGG GCTCTGCTGT TAGCCTTTCT -3255  (780)
CTGGCAGCAG GACAGGCTCA TCCCTCTTAT CAGACAGGCT GGACTTGGTG GAAGTTGAC  -3195  (840)
ACTCTGGGGG CGGCCTTCAT GGATAAATAC TGTAGTTTTC TTGCCCCTCA AGTGAGACAA -3135  (900)
CCCCAAGGCG TGCTCTGTGC AGTCTCCCGA GGCCCCACC AGGGCTGAGC ACCTGTTTCC  -3075  (960)
CCAGCAGCAA GTGCTCCTTA ATCTACTTTC TCCTGGTTTC CTTCCCTTTG CTGTCTC    -3018  (1020)
```

DIAGNOSIS OF ATTENTION DEFICIT HYPERACTIVITY DISORDER

CROSS-REFERENCE TO RELATED APPLICATION

This application claims benefit of U.S. Provisional Application No. 60/773,459, filed Feb. 15, 2006, which is incorporated by reference in its entirety.

STATEMENT OF FEDERALLY SPONSORED RESEARCH

This invention was funded by grants MH48866 and DC006501 from the National Institute of Health. The government may have certain rights in the invention.

FIELD OF THE INVENTION

The present invention relates to the field of neurological and neuropsychiatric disorders.

BACKGROUND OF THE INVENTION

Noradrenergic neurons in the brain project into all parts of the neuraxis and regulate many functions of the nervous system, including memory, attention, emotion, and autonomic function. The norepinephrine transporter (NET) is primarily responsible for reuptake of norepinephrine (NE) into presynaptic nerve terminals, thus regulating both its transmission and homeostasis (1, 2). The NET belongs to a superfamily of $Na^+/Cl^-$-dependent transporters (3). The human NET (hNET) gene, spanning approximately 45 kb, is located on chromosome 16q12.2 (4). Genomic clones and cDNA encoding the human NET (hNET) have been isolated and characterized, thus making possible molecular investigation of regulatory mechanisms of NET gene expression (5).

Given the global role of NE in the CNS and PNS, dysfunction of the NE system may underlie various pathological conditions such as neurodegenerative, psychiatric, and endocrine disorders. Particularly, the gene encoding NET has been speculated to play a role in diverse psychiatric and autonomic disorders. For example, in patients suffering from major depression, the levels of NET, measured by brain imaging and binding techniques in post mortem brain samples, have been shown to be altered (6). The NET is reported to be a target of the tricyclic antidepressant drugs. In addition, the NET is reported to be a potential therapeutic target for treating post-traumatic stress disorder, social anxiety disorder, and eating disorder (7).

Several polymorphisms in the coding and non-coding regions of NET have been described. At present, there are about 20 known naturally occurring missense mutations in the coding region of hNET (10). These include several variants with impaired glycosylation and are decreased in surface expression, features that have been reported to influence the transporter function by altering its biosynthesis and trafficking (10, 11). An individual suffering from orthostatic intolerance, tachycardia, and elevated plasma NE levels recently has been reported to have a missense mutation (Ala457Pro) in the highly conserved transmembrane domain 9 of the NET (12). Further, a polymorphic region in the non-coding region was reported to be associated with anorexia nervosa (13).

SUMMARY OF THE INVENTION

This invention is based on the discovery of a novel polymorphism, −3081(A/T), which is located in the promoter of the human norepinephrine transporter (hNET) gene. This polymorphism causes a reduction in the expression of hNET and is associated with attentional disorders, including the inattentive subtype of ADHD. The rare T-allele at −3081 creates an E2 box motif CACCTG not present in the more prevalent A-allele. The human Slug (hSlug) and human Scratch (hScratch) proteins, known transcriptional repressors, bind to this E2 box motif in the hNET promoter and inhibit or reduce hNET expression.

Accordingly, the invention features a substantially pure nucleic acid fragment of 4 kb or less, wherein the nucleic acid fragment consists of a nucleotide sequence that is substantially identical (e.g., 90%, 95%, 97%, 99%, or 100% identical) to nucleotides 943 through 963 of SEQ ID NO. 2. In one embodiment, nucleotide 954 of SEQ ID NO.:2 (corresponding to −3081 of the hNET gene as shown in FIG. 7) is not adenine (e.g., thymine, cytosine, and guanine). In another embodiment, nucleotide −3081 of the hNET gene (see FIG. 7) is thymine. In another embodiment, the substantially purified nucleic acid fragment comprises an E2 box motif. In another embodiment, the substantially purified nucleic acid fragment is capable of binding to a Snail superfamily protein including, for example, a Slug or Scratch protein (e.g., hSlug or hScratch). More particularly, the substantially purified nucleic acid fragment of this aspect of the invention are at least about 10, 15, 20, 25, 30, 35, 40, 50, 100, or more nucleotides in length.

In another aspect, the invention features a substantially pure nucleic acid fragment of 4 kb or less, having a nucleotide sequence that is complementary to at least 6 contiguous nucleotides between 943 and 965 of SEQ ID NO.:2 (corresponding to −3070 and −3092 of the hNET gene). In one embodiment, corresponding to position 954 of SEQ ID NO.:2 is not thymine. In another embodiment, corresponding to nucleotide 954 of SEQ ID NO.:2 is adenine. Preferably, the nucleic acid is at least 10, 12, 15, 20, 25, 30, 35, 40, 50, 100, or more nucleotides in length.

In another aspect, the invention provides a method for diagnosing a subject as having an increased likelihood of developing an attentional disorder (e.g., attention deficit hyperactivity disorder (ADHD)), wherein the subject is positively diagnosed as having an increased likelihood when −3081 hNET is not adenine (e.g., −3081 hNET, as shown in FIG. 7, is thymine, cytosine, guanine). In some embodiments, the method comprises using one or more analytical methods including, for example, polymerase chain reaction (PCR), restriction fragment length polymorphism (RFLP) analysis, nucleotide sequencing, nucleotide sequencing by primer extension, and allele-specific PCR (ASPCR). In one embodiment, RFLP is performed using BsrI. In one specific embodiment, the method has the following steps: (a) obtaining DNA from the subject; (b) amplifying a region of said DNA, wherein the region contains −3081 hNET; (c) identifying whether −3081 hNET is adenine (e.g., thymine); and (d) diagnosing the subject as having an increased likelihood of developing an attentional disorder when said nucleotide is not adenine. In one embodiment, the diagnosis is for an increased likelihood of the inattentive subtype of ADHD.

In a related aspect, the invention provides a method for confirming a diagnosis of an attentional disorder in a subject comprising determining whether the nucleotide base at −3081 hNET is not adenine (e.g., thymine).

The invention also provides a method for identifying a candidate compound that is useful for increasing hNET expression or for treating an attentional disorder. In one embodiment, the method comprises the steps of:

(a) providing a cell comprising a promoter having at least 20 nucleotides that are at least 95% identity to nucleotides 943 through 963 of SEQ ID NO.:2, wherein the nucleotide base corresponding to position 954 is thymine and said promoter is operably linked to a protein coding sequence;

(b) contacting said cell with a candidate compound; and (c) assessing the level of expression of the protein coding sequence relative to the level of expression of the protein coding sequence in the absence of the candidate compound, wherein a candidate compound that increases the level of expression of the protein is identified as a compound useful for increasing hNET expression or treating an attentional disorder.

In one embodiment, the assessing step comprises measuring the transcription product (e.g., RNA) of the protein coding sequence or measuring the level of expression of the protein encoded by the protein coding sequence using, for example, receptor binding assays or Western blot analysis. In another embodiment, the protein coding sequence encodes an hNET protein. Alternatively, the protein coding sequence comprises a reporter gene including, for example, luciferase and chloramphenicol acetyltransferase (CAT). In other embodiments, the promoter comprises an E2 box motif and/or is capable of binding to a Slug or Scratch protein (e.g., hSlug or hScratch) and/or the cells further expresses a Slug or Scratch protein (e.g., hSlug or hScratch). Suitable cell types include, for example, nor-adrenergic cells and neuroblastoma cells.

In another aspect, the invention provides a method for identifying a candidate compound that is useful for increasing hNET expression or treating an attentional disorder, the method comprising the steps of:

(a) providing a cell comprising a promoter, wherein the promoter comprises an E2 box motif and is operably linked to a protein coding sequence;

(b) contacting the cell with a candidate compound; and (c) assessing the level of expression of the protein coding sequence relative to the level of expression of the protein coding sequence in the absence of said candidate compound, wherein a candidate compound that increases the level of expression is identified as a compound useful for increasing hNET expression or treating an attentional disorder.

In some embodiments, the E2 box motif comprises the nucleotide sequence CACCTG. In other embodiments, the cells further express a basic helix-hoop-helix protein including, for example, Snail superfamily proteins, such as a Slug or Scratch protein (e.g., hSlug and hScratch).

In another aspect the invention provides a method for identifying a candidate compound that is useful for increasing hNET expression or treating an attentional disorder, having the steps of: (a) providing a sample containing (i) a nucleic acid having an E2 box motif and (ii) a protein capable of binding the E2 box motif; (b) contacting the sample with a candidate compound; and (c) assessing the binding of the protein to the nucleic acid in the sample in the presence of the candidate compound relative to binding in the absence of the candidate compound, wherein a candidate compound that decreases the level of binding is identified as a compound useful for increasing hNET expression or treating an attentional disorder. Useful proteins include helix-loop-helix proteins such as, Snail superfamily proteins including, for example, a Slug or Scratch protein (e.g., hSlug and hScratch). In specific embodiments, the nucleic acid contains the nucleotide sequence CACCTG.

The invention also provides a method for treating an attentional disorder in a patient by increasing the expression of hNET in said patient. Preferably, the patient is diagnosed as having a mutation at hNET −3081 (e.g., hNET −3081(T)). The therapeutic method may include administering a compound that increases transcription of the −3081(T) hNET gene. This may occur by, for example, inhibiting Slug or Scratch (e.g., hSlug or hScratch) binding to the 5'-untranslated region of the hNET gene, administering a compound capable of inhibiting Slug binding or Scratch binding to an E2 box motif, administering a compound capable of inhibiting hSlug binding or hScratch binding to CtBP-1, or administering an hSlug-specific or an hScratch-specific RNAi. Alternatively, hNET expression may be increased by administering a vector capable of expressing an hNET protein. In preferred embodiments, such a vector would be administered to the brain (e.g., by stereotactic or intraventricular injection). In other embodiments, the hNET protein is expressed by nor-adrenergic neurons in the brain.

The invention also provides a method for increasing the expression of hNET in a patient. Patients for whom increased expression of hNET may be desirable include, for example, patients diagnosed as having an attentional disorder (e.g., ADHD) and patients diagnosed as having a mutation at hNET −3081 (e.g., hNET −3081(T), as shown in FIG. 7). The therapeutic method may include administering a compound that increases transcription of the −3081(T) hNET gene. This may occur by, for example, inhibiting Slug or Scratch (e.g., hSlug or hScratch) binding to the 5'-untranslated region of the hNET gene, administering a compound capable of inhibiting Slug binding or Scratch binding to an E2 box motif, administering a compound capable of inhibiting Slug binding or Scratch binding to CtBP-1, or administering a Slug-specific or a Scratch-specific RNAi. Alternatively, hNET expression may be increased by administering a vector capable of expressing an hNET protein. In preferred embodiments, such a vector would be administered to the brain (e.g., by stereotactic or intraventricular injection). In other embodiments, the hNET protein is expressed by nor-adrenergic neurons in the brain.

In another aspect, the invention provides a method of predicting the efficacy in a patient of therapeutic inhibitors of hNET, comprising determining if the individual has a mutation at hNET −3081 (e.g., when −3081 hNET is not adenine). This predictive method is useful in patients having any disease related to altered synaptic levels of norepinephrine, but particularly attentional disorders including, for example, ADHD (e.g., the inattentive subtype). The predictive method is also useful with any hNET inhibitor including, for example, hNET-selective inhibitors such as atomoxetine and reboxetine, and mixed inhibitors such as clovoxamine, duloxetine, nefazodone, sibutramine and venlafaxine. In one embodiment, the patient is identified as having −3081(T).

As used herein, "attentional disorder" refers to disorders characterized by developmentally inappropriate degrees of inattention, overactivity, and impulsivity, such as Attention Deficit Hyperactivity Disorder (ADHD), Attention Deficit Disorder (ADD), and Hyperkinetic Disorder. Attention Deficit Hyperactivity Disorder is a disorder characterized by inattention, impulsiveness, and hyperactivity. This disorder can impair social function, learning and/or development and is therefore now recognized as a serious problem. It is further recognized that many children with ADHD go on to develop other co-morbid conditions or social problems in adulthood. ADHD is diagnosed if any one of the three main clinical features (inattention, over-activity, and impulsiveness) persists in two or more social situations, e.g., in both a home and school environment (American Psychiatric Association. Diagnostic and Statistical Manual of Mental Disorders, Fourth Edition (DSM-IV) Washington D.C.; American Psychiatric Association, 1994). A diagnosis of Hyperkinetic Disorder is made only if all three of the main clinical features have been present from an early age, persist in more than one social situation (e.g. home and school), and impair function (The ICD-10 Classification of Mental and Behavioural Disorders: Diagnostic Criteria for Research. Geneva: World Health Organisation, 1993: 155-7).

The terms "hNET," and "human nor-epinephrine transporter" refer to the gene or gene product of the human solute carrier family 6, member 2 (SLC6A2) gene located on chromosome 16q12.2 (4; also see, for example, GenBank accession no. AF061198).

The terms "−3081 hNET," "nucleotide −3081 of the hNET gene" and terms of like content refer generically to the specified position in the hNET gene which is in the 5'-UTR region of the hNET gene, such as shown in FIG. 7. This nucleic acid position corresponds to position 954 of SEQ ID NOs: 1 and 2. Also included within meaning of these terms are sequences which are substantially identical to the sequence shown in FIG. 7 and which include the position seen in −3081 of the hNET gene.

The terms "−3081(A)" and "−3081(T)" refer to specific hNET alleles and substantially identical polynucleic acids which contain an adenine or thymine, respectively, at the nucleotide position that corresponds to −3081 as shown in FIG. 7.

As used herein, the term "hSlug" refers to the human "Snail homolog 2" gene located on chromosome 8 at location 8q11 and identified officially as SNAI2 (Entrez Gene ID No. 6591). The mRNA sequence of hSlug may be found, for example, at Genbank Accession Nos. NM_003068 and U97060, and protein sequence at NP_003059 (also see, for example, Savagner et al., J. Cell. Biol. 137: 1403-1409, 1997 and other references cited herein). Other features of hSlug are described herein.

As used herein, the terms "Slug protein" and the like refer to homologs from non-human species including, for example, homologs from the mouse, rat, chicken, zebrafish (*Danio rerio*), and Xenopus. Also included are fragments of Slug proteins that retain a DNA binding capability (e.g., capability to bind to an E2 box motif).

As used herein, the terms "Scratch protein" and the like refer to homologs from non-human species including, for example, homologs from the mouse, rat, zebrafish (*Danio rerio*), cow (*Bos taurus*), and dog (*Canis familiaris*). Also included are fragments of Scratch proteins that retain a DNA binding capability (e.g., capability to bind to an E2 box motif).

As used herein, the term "hScratch" refers to the human "Scratch homolog 1" gene located on chromosome 8 at location 8q24.3 and identified officially as SCRT1 (Entrez Gene ID No. 83482). The mRNA and protein sequence of hScratch may be found, for example, at Genbank Accession Nos. AY014996 and AAK0467.1, respectively (also see, for example, Nakakura et al., Proc. Natl. Acad. Sci. USA 98: 4010-4015, 2001).

By "substantially identical" is meant a nucleic acid exhibiting at least 75%, but preferably 85%, more preferably 90%, most preferably 95%, or even 99% identity to the reference nucleic acid sequence. The length of comparison sequences will generally be at least 20 nucleotides, preferably at least 50 nucleotides, and more preferably at least 100 nucleotides.

By "substantially pure" is meant a nucleic acid, polypeptide, or other molecule that has been separated from the components that naturally accompany it. Typically, the molecule is substantially pure when it is at least 60%, 70%, 80%, 90% 95%, or even 99%, by weight, free from the proteins, nucleic acids, and naturally-occurring organic molecules with which it is naturally associated. A substantially pure nucleic acid, for example, also may be one which is free from all other nucleic acids.

By "operably linked" is meant that a nucleic acid molecule and one or more regulatory sequences (e.g., a promoter) are connected in such a way as to permit expression and/or secretion of the product (e.g., a protein) encoded by the nucleic acid molecule when the appropriate accessory molecules (e.g., transcriptional activator proteins), if necessary, are bound to the regulatory sequences.

By "therapeutically effective amount" is meant a quantity of compound delivered with sufficient frequency and in a sufficient amount to provide a medical benefit to the patient. For example, a therapeutically effective amount of a composition of this invention is an amount sufficient to treat or ameliorate at least one adverse effect or symptom of ADHD.

By "treating" is meant administering a pharmaceutical composition for the propose of improving the condition of a patient by reducing, alleviating, or reversing at least one adverse effect or symptom.

BRIEF DESCRIPTION OF DRAWINGS

FIG. 2A is a pair of graphs showing the −3081(A/T) polymorphism of the hNET promoter. The reverse complement sequences from −3072 to −3090 of hNET promoter is shown. (SEQ ID NOS 7-8, respectively, in order or appearance). The asterisk indicates the polymorphic change. FIG. 2B is an electrophoretic gel showing the A/T polymorphism at position −3081.

FIG. 3A is a series of bar graphs showing the relative CAT activity produced by constructs comprising the sequence between −4000 and −3018 containing either A or T at −3081 bp. These constructs were subcloned in antisense orientation 5' of the pNET133(i)CAT. The normalized CAT activities driven by an A allele containing construct in each cell line was set to 100 to compare the relative strength of a T allele containing construct. Significant differences between A and T alleles were evaluated by unpaired t test with two-tailed p values: *p<0.05, p<0.005, *p<0.0005. FIG. 3B is a series of bar graphs showing the relative luciferase activity produced by constructs having 4 kb upstream sequence and the first intron of the hNET gene which were inserted upstream of the luciferase coding sequence in the pGL3 basic (Promega) vector. The constructs were transiently transfected into identified cell lines. FIG. 3C is a series of bar graphs showing the relative luciferase activity of constructs containing six copies of the hNET oligonucleotide containing A (SEQ ID NO: 9) or T (SEQ ID NO: 10) alleles that were coupled to a heterologous TK promoter and a luciferase reporter gene. To compare luciferase activities between two constructs, luciferase activity driven by TK promoter was set to 100.

FIG. 5A is a gel showing the result of an EMSA showing that hSlug and hScratch, but not δ-EF1 or Snail, bind to the −5081(T) hNET promoter allele. None of the these DNA binding proteins bound to the −5081(A) promoter allele.

FIG. 7A is the wildtype nucleic acid sequence of a portion of the 5'-UTR of the hNET gene (SEQ ID NO.:1). The wildtype allele comprises −3081(A). FIG. 7B is the mutated hNET 5'-UTR comprising the −3081(T) allele (SEQ ID NO.: 2). The numbers in parenthesis indicate the nucleotide numbering as it appears in the Sequence Listing.−3081 hNET corresponds to nucleotide 954.

DETAILED DESCRIPTION

This invention is based on the discovery of an A/T polymorphism at −3081 upstream of human NET (hNET) gene, the product of which regulates both neurotransmission and homeostasis of norepinephrine (NE) in the nervous system. Position −3081 is located in the promoter and upstream of the transcription initiation site. The −3081(T) allele significantly reduces promoter function compared to the more prevalent −3081(A) allele and creates a palindromic E2 box motif that binds to the (human) Snail superfamily proteins hSlug and hScratch, both of which are transcriptional repressors. Coexpression of hSlug or hScratch with the hNET promoter bearing the −3081(T) allele significantly represses hNET promoter activity compared to the −3081(A)-containing hNET promoter. Presence of the −3081(T) allele in the hNET gene was found to be associated with the inattentive subtype of ADHD (iADHD).

Noradrenergic Cell-Specific Expression of the hNET Gene

Figure 1:
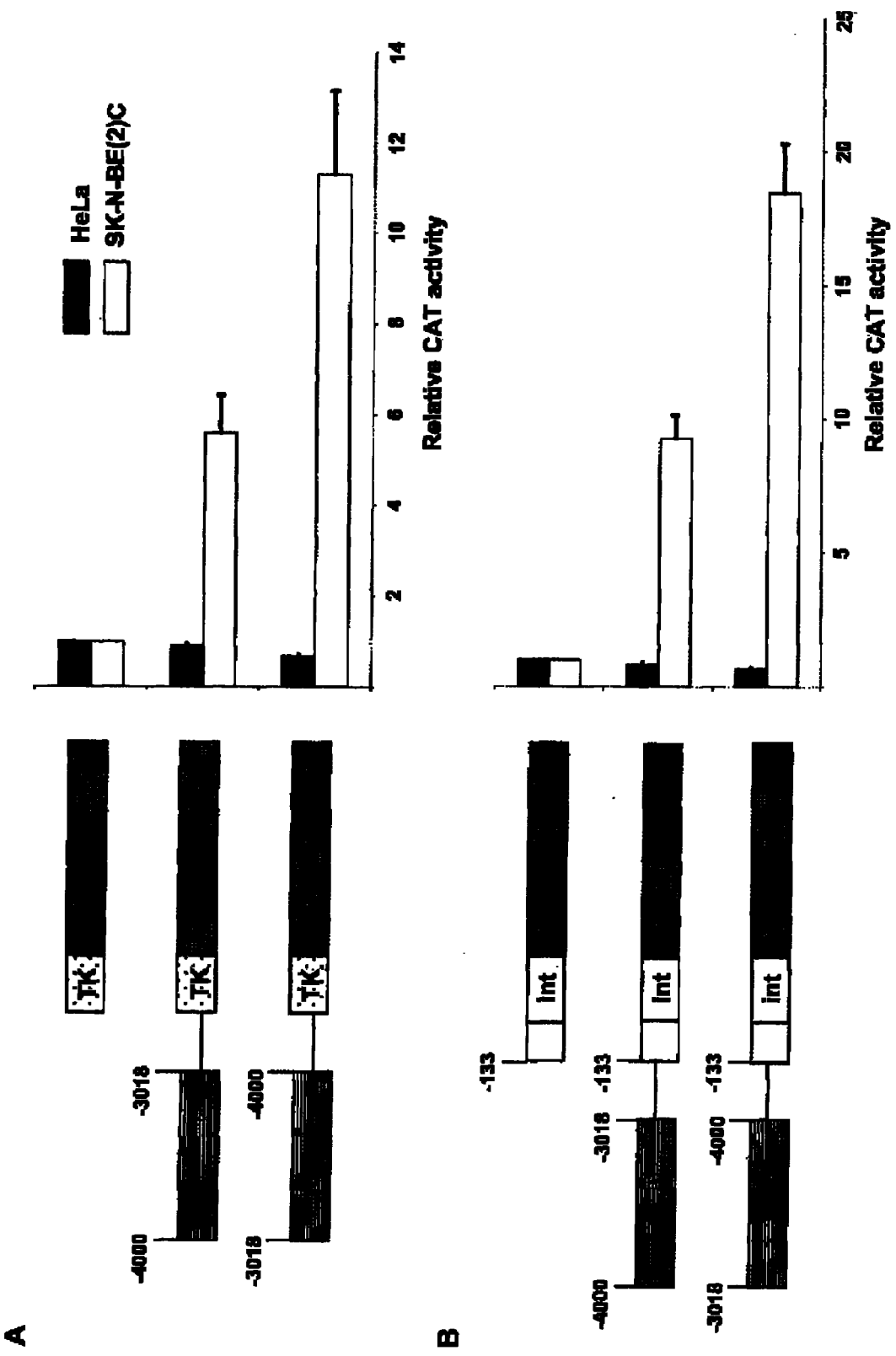
FIG. 1 is a series of bar graphs demonstrating that the sequence between −4000 and −3018 of the hNET promoter contains the noradrenergic cell-specific transcriptional element. The fragment comprising the sequence between −4000 and −3018 was subcloned in either sense or antisense orientation 5' of the pBLCAT2 (FIG. 1A) or 5' of the pNET133(i) CAT (FIG. 1B) previously described (14).

The distal promoter region at −4.0 to −3.1 kb contains a noradrenergic-specific enhancer, whereas a silencer domain seems to be located between −3.1 kb and −133 bp (14). The fragment comprising the sequence between −4000 and −3018 was subcloned in either sense or antisense orientation 5' of the pBLCAT2 (FIG. 1A) or 5' of the pNET133(i)CAT (FIG. 1B) previously described (14). The reporter constructs were transfected into the NET-positive SK-BE(2)C cells and NET-negative HeLa cells, and the normalized CAT activity of each construct was expressed relative to the vector pBLCAT2 and pNET133(i)CAT, respectively. This domain of the hNET promoter increased TK promoter activity in both sense and anti-sense orientations in SK-N-BE(2)C cells and did so in either orientation (sense and anti-sense). In contrast, no such effect was observed in HeLa cells, demonstrating that this domain has characteristics of a noradrenergic cell-specific enhancer.

Identification of a Polymorphism in the hNET Upstream Enhancer Domain

The upstream enhancer domains of the region encompassing from −−4000 to −3018 bp were amplified with 60 independent genomic DNA samples and analyzed them by DNA sequencing. This analysis revealed one common polymorphism at −3081(A/T) (FIG. 2).

The −3081(T) Polymorphism is Associated with ADHD

The Kiddie-SADS Present and Lifetime Version (30) was used to determine that DSM-IV criteria for the predominantly Inattentive or Combined subtypes of ADHD were met (31). Buccal cell samples were collected from subjects between the ages of 6 and 17 years and from age- and ethnicity-matched controls. Genomic DNA was analyzed for the presence of the −3081(A/T) polymorphism. The single nucleotide polymorphism (SNP) was genotyped by PCR-RFLP analysis (see FIG. 2).

A 148 bp region containing nucleotides −3165 to −3018 of the human NET gene was amplified by PCR with primers NET137S (5'-CTGTAGTTTTCTTGCCCCTCAAG-3'; SEQ ID NO.:3) and NET38A. The PCR fragment was then digested with 5 units of restriction endonuclease BsrI at 65° C. for 2 hrs for −3081(A/T). Digestion products were run on 7% polyacrylamide gels or 3% NuSieve agarose gels stained with ethidium bromide for imaging under UV light.

Ninety four (94) patients who met DSM-IV criteria for ADHD and in 60 unaffected controls were tested for the −3081(A/T) hNET polymorphism in order to determine whether that polymorphism is associated with childhood ADHD. Screening was done by SNP genotyping using PCR-RFLP analysis. The data were evaluated for statistical significance using nominal p-values, but also examined significance using permutation tests given our sample size. The permutation-based significance levels were only slightly higher than standard p-values (i.e., ~5-10%), and thus did not materially alter any conclusion regarding the associations between ADHD and the −3081(A/T) SNP. It was first established that this SNP was in Hardy-Weinberg equilibrium using a simulation-based method (49) in the full sample ($\chi^2$=0.59, p=0.566), as well as separately in cases ($\chi^2$=0.35, p=0.711) and controls ($\chi^2$=0.001, p=1.000). The frequency of the −3081(T) allele in ADHD cases was 0.37 compared with 0.22 in controls, a statistically significant difference ($\chi^2$=7.07, p=0.008, OR=2.00, 95% CI=1.19-3.37). Differences in the genotypes of ADHD cases and controls were also significant (logistic regression results for the linear trend contrasting the number of T alleles: $\chi^2$=6.49, p=0.011, $R^2$=0.06). Similar to the allele-wise results, the AT and TT genotypes were overrepresented in ADHD cases whereas the AA genotype was over-represented in controls (ADHD cases: AA=0.42, AT=0.44, TT=0.15; controls: AA=0.60, AT=0.35, TT=0.05).

A potential confound in case-control studies of association is population stratification biases, which are most commonly due to the sampling of individuals from different ethnic backgrounds that vary in both allele frequencies at the tested marker and in rates of the disorder being studied (25, 26). A search of the HapMap database (50) revealed substantial allele frequency differences between the European-American and African-American samples for many of the SNPs in hNET, suggesting the need to control for ethnic background in testing for association between SNPs in this gene and ADHD. There were significant differences in allele frequency between individuals of African-American background and those of European-American, Hispanic, or Asian ethnicity (TABLE 1) ($\chi^2$=15.50, p<0.001, OR=4.85, 95% CI=2.08-11.36), such that the frequency of the T allele was 0.65 in individuals of African-American background as compared with 0.28 in individuals of European-American, Hispanic, or Asian ethnicity. Similar differences were observed for the comparison of genotype frequencies between individuals of African-American and the other ethnic backgrounds ($\chi^2$=19.11, p<0.001, $\phi$=0.35). In contrast, no such differences were observed among the individuals of European-American, Hispanic, or Asian ethnicity ($\chi^2$=2.21, p=0.696, $\phi$0.12), indicating that these groups could be combined in the subsequent case-control analyses in which ethnicity was controlled (TABLE 1).

TABLE 1

Genotype Differences Between African-American Children of and Children of Other Ethnicity

| | | | Genotype | | | |
|---|---|---|---|---|---|---|
| | | | AA | AT | TT | Total |
| Ethnicity | Asian | Count | 3 | 1 | 0 | 4 |
| | | % within ethnicity | 75.0% | 25.0% | .0% | 100.0% |
| | African-American | Count | 2 | 5 | 6 | 13 |
| | | % within ethnicity | 15.4% | 38.5% | 46.2% | 100.0% |
| | Hispanic | Count | 7 | 5 | 0 | 12 |
| | | % within ethnicity | 58.3% | 41.7% | .0% | 100.0% |
| | European-American | Count | 63 | 51 | 11 | 125 |
| | | % within ethnicity | 50.4% | 40.8% | 8.8% | 100.0% |
| Total | | Count | 75 | 62 | 17 | 154 |
| | | % within ethnicity | 48.7% | 40.3% | 11.0% | 100.0% |

The clinic samples were collected at two independent sites, making it necessary to control for any possible heterogeneity across site (TABLE 2). After removing individuals of African-American ethnic background from the sample, genotype differences were found between the cases sampled from Vanderbilt and McLean Hospital ($\chi^2$=9.88, p=0.007, $\phi$=0.35). (Similar analyses using logistic regression in which ethnicity was controlled yielded virtually identical results).

TABLE 2

Genotype Differences Among Control Subjects Based on Clinical Trial Location

| | | | Genotype | | | |
|---|---|---|---|---|---|---|
| | | | AA | AT | TT | Total |
| Site | Emory Controls | Count % | 36 60.0% | 21 35.0% | 3 5.0% | 60 100.0% |
| | McLean ADHD Cases | Count % | 7 26.9% | 12 46.2% | 7 26.9% | 26 100.0% |
| | Vanderbilt ADHD Cases | Count % | 32 47.1% | 29 42.6% | 7 10.3% | 68 100.0% |
| Total | | Count % | 75 48.7% | 62 40.3% | 17 11.0% | 154 100.0% |

Given the heterogeneity that was observed due to both ethnic background and clinic site, the association presented above (between ADHD and the −3081(A/T) SNP after removal of the 13 individuals of African-American ethnic background and controlling for clinic site) was reanalyzed. Differences in the genotypes of ADHD cases and controls remained significant after removal of the individuals of African-American ethnic background and when clinical site was controlled via its inclusion as a covariate in the analyses (logistic regression results for the linear trend contrasting the number of T alleles: $\chi^2$=4.79, p=0.029, OR=3.38, 95% CI=1.14-10.10, $R^2$=0.06). Similar to the results above, the AT and TT genotypes were still over-represented in ADHD cases whereas the AA genotype was over-represented in controls.

Effect of the −3081(A/T) Polymorphism on Promoter Activity

The functional effect of this polymorphism on the hNET enhancer activity was assessed. Constructs having the enhancer domain from −4000 to −3018 with A or T allele at nucleotide position −3081 in front of the NET proximal promoter (designated as pNETB(A)133(i)CAT and pNETB(T)133(i)CAT, respectively) were subcloned and examined for transcriptional activity in human neuroblastoma cell lines SK-N-BE(2)C and SK-N-BE(2)M17.

Human neuroblastoma SK-N-BE(2)C and SK-N-BE(2)M17 cells were maintained as previously described (14).

Transfections were performed using Lipofectamine™ (Invitrogen). Plasmids for transfection were prepared using Qiagen columns (Qiagen). One day before transfection, cells were plated in individual wells of 24-well plates at a density of $9\times10^4$ cells per well. For the SK-N-BE(2)C and SK-N-BE(2) M17 cell-lines, each well was transfected with an equimolar amount (0.1 pmol) of each reporter construct, 0.125 μg of pRSV-βgal, and pUC19 plasmid for a total of 0.625 μg DNA. In cotransfection analysis, a half molar amount of the reporter construct was used for the pCMV-Slug. Cells were harvested 24 to 48 h after transfection, and assayed for luciferase activity. All experiments were done in triplicate and repeated three to six times with different DNA preparations. To correct for differences in transfection efficiencies, luciferase or CAT activity was normalized to β-galactosidase activity.

Figure 3:
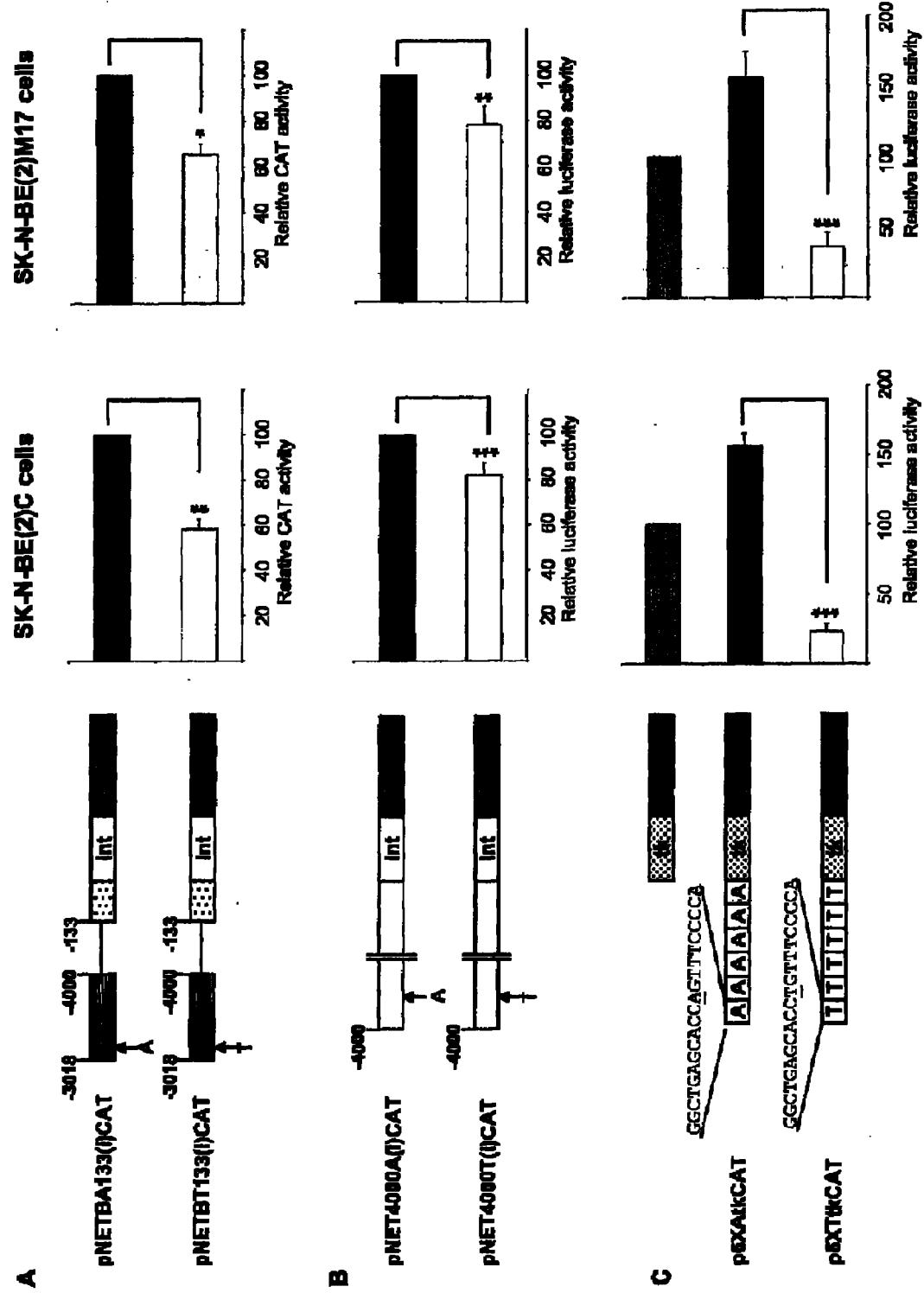
FIG. 3 is a series of reporter constructs based on the −3081 (A/T) polymorphism and their accompanying reporter gene activity levels.

Reporter gene expression driven by the −3081(T) allele construct was reduced by 50% compared to the wild type construct (p<0.005) (FIG. 3A). A 4 kb upstream sequence containing the −3081(A) or −3081(T) alleles was cloned into a luciferase reporter plasmid, and the activity was measured in the human neuroblastoma cell lines, SK-N-BE(2)C and SK-N-BE(2)M17. The NET4000T(i)LUC(T) (having −3081 (T)) resulted in a 25% and 28% reduction of basal promoter activity in SKN-BE(2)C and SK-N-BE(2)M17, respectively, compared with pNET4000A(i)LUC(A) (having −3081(A)) (FIG. 3B).

In another experiment, reporter constructs having six copies of an oligonucleotide containing −3092 to −3072 of the hNET gene promoter bearing either nucleotide A or T at −3081 were placed in front of the TK promoter. These reporter constructs were then used in transient transfection assay in SK-N-BE(2)C and SK-N-BE(2)M17 cells. The reporter construct with nucleotide A at −3081 slightly stimulated TK promoter activity; whereas, the reporter construct with nucleotide T at −3081 decreased TK promoter activity by 85% to 70% in SK-N-BE(2)C and SK-N-BE(2)M17 cells, respectively (p<0.0005) (FIG. 3C).

DNA-Protein Interaction at a Palindromic Sequence Motif Containing −3081(T)

The ability of the −3081(T) mutation to interact with DNA-binding proteins in cell nuclear extracts was investigated, Nuclear extracts were prepared from SK-N-BE(2)C and HeLa cells (14). The pellet was resuspended in buffer D (20 mM HEPES, pH7.9, 20% glycerol, 0.1M KCl, 0.2 mM PMSF, and 0.5 mM DTT) and dialyzed against the same buffer, The extracts were quick-frozen in liquid nitrogen and aliquots stored at −70° C. and used within 3 months of extraction.

The −3081(A/T) oligonucleotides were synthesized with either the A or T variant centrally located and annealed to produce double stranded DNA (5'-GGCTGAGCACC(A/T) GTT TCCCA-3'; SEQ ID NO.:4), and $^{32}$P-labeled by T4 DNA kinase. For electromobility shift assays (EMSA), competition-binding assays were performed by adding non-radioactive competitor oligonucleotides in molar excess before adding $^{32}$P-labeled oligonucleotides. For Supershift assays, antibodies were co-incubated with the nuclear extract mix for 30 min at 4° C. before adding the radiolabeled probe. Antibodies against Slug and Snail were purchased from Santa Cruz Biotechnology (Santa Cruz, Calif.). Antibody against δEF1 was provided by Dr. Hisato Kondoh (Osaka University, Japan).

Figure 4:
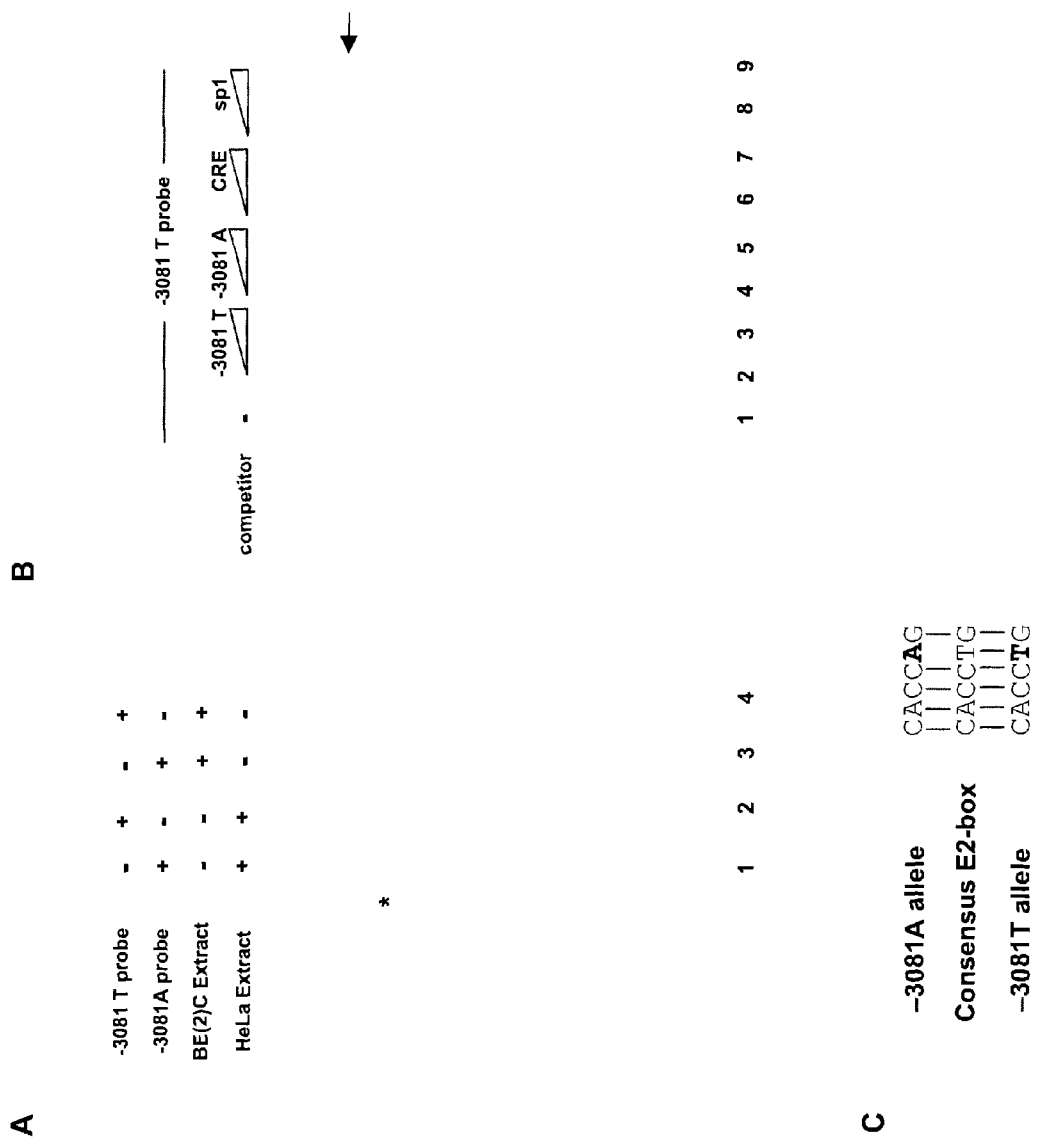
FIG. 4A is a gel showing the results of electromobility shift assay (EMSA) that were conducted using nuclear extracts from SK-N-BE(2)C and HeLa cells with labeled probes for the allele A (lane 1 and 3) and for the allele T (lane 2 and 4). An allele-specific complex was indicated by the arrow at right. A non-specific complex was shown by the asterisk.
FIG. 4B is a gel showing the result of electromobility shift assay (EMSA) that were performed using nuclear extracts from SK-N-BE(2)C cells with $^{32}$P-labeled oligonucleotide containing allele T. This DNA-protein complex was competed by unlabeled −3081(T) oligonucleotide, but not by either −3081 (A) or the unrelated CRE and sp1 oligonucleotides.
FIG. 4C is a schematic representation of E2 box DNA sequence created by polymorphism at −3081.

A single major DNA-protein complex was detected when a −3081(T) allele probe, but not the −3081(A) allele probe was contacted with nuclear extracts from HeLa or SK-N-BE(2)C cells (FIG. 4A). Formation of this DNA-protein complex demonstrates that −3081(T) creates a new nuclear protein binding site in the hNET promoter.

In a competition assay, formation of the DNA-protein complex was diminished by unlabeled −3081(T) oligonucleotide, but not by −3081(A) or the unrelated CRE and Sp1 oligonucleotides (FIG. 4B). This demonstrates specific DNA-protein complex formation with the −3081(T) allele.

A search of the TRANSFAC database for known transcription factor binding motifs revealed that the −3081(T) polymorphism, but not the −3081(A) polymorphism contains an E2-box motif (CACCTG) (FIG. 4C), which is a known binding site for the basic helix-loop-helix class of transcription factors.

hslug and hScratch Proteins Interact with E2 Box Element Created by −3081T Polymorphism Transcription regulators called δEF1/ZEB, Snail, Scratch, and Slug have been reported both to bind to a consensus E2 box (CACCTG) and function as potential transcriptional repressors (16, 17). The δEF1/ZEB contains two clusters of Krüppel type zinc fingers in the N- and C-terminus and one homeodomain in the middle (16), whereas Snail, Scratch, and Slug, members of the Snail family, have four to six zinc fingers in the C-terminus region (17). These transcription factors are involved in mesodermal cell fate and neural crest development.

An electromobility shift assay (EMSA) was performed using in vitro translated hδEF1/ZEB, hSnail, hScratch, and hSlug proteins. Incubation of recombinant forms of δEF1/ZEB and Snail produced no complexes with oligonucleotide probe containing either the A or T allele. (FIG. 5A). Recombinant hSlug and hScratch, however, generated a single complex with the oligonucleotide probe containing the T allele but not the A allele (FIG. 5A).

Figure 5B:
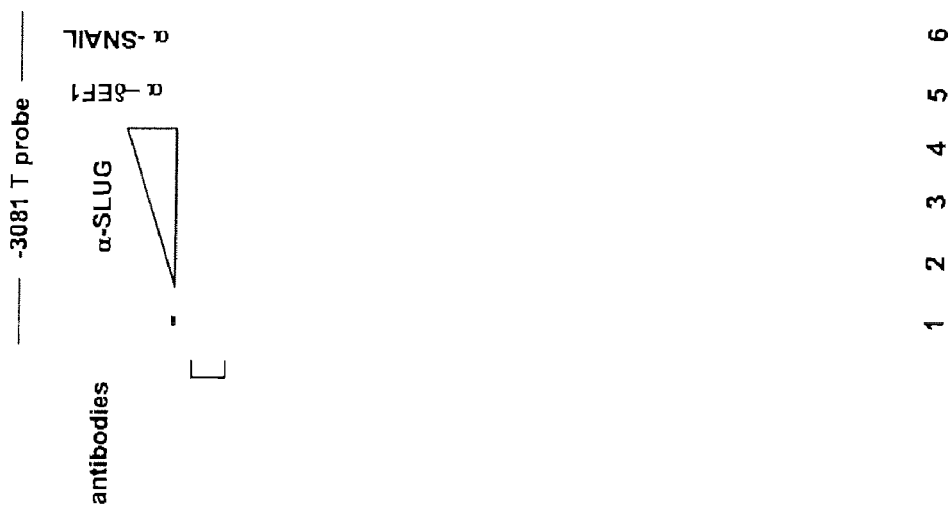
FIG. 5B is a gel showing the result of an EMSA using antibodies against specific transcriptional repressors known to bind the E2 box consensus sequence. hSlug, but neither Snail nor δ-EF1, binds to the E2 box generated by the polymorphism at −3081 of the hNET gene. The −3081(T) oligonucleotide radiolabeled probe was incubated with SK-N-BE(2)C nuclear extract in the absence (lane 1) or presence of antibodies (lane 2-6). Coincubation of nuclear proteins with increasing amounts of Slug-specific antibody 0.2 μg (lane 2), 0.5 μg (lane 3), and 1 μg (lane 4) resulted in the generation of a supershifted band in a dose-responsive manner (arrow). In addition, formation of DNA-protein complex was significantly diminished. In contrast, co-incubation with δ-EF1 or Snail-specific antibody (1 μg each) neither generated the supershifted band nor diminished formation of DNA-protein complex (lane 5, 6).
Figure 5C:
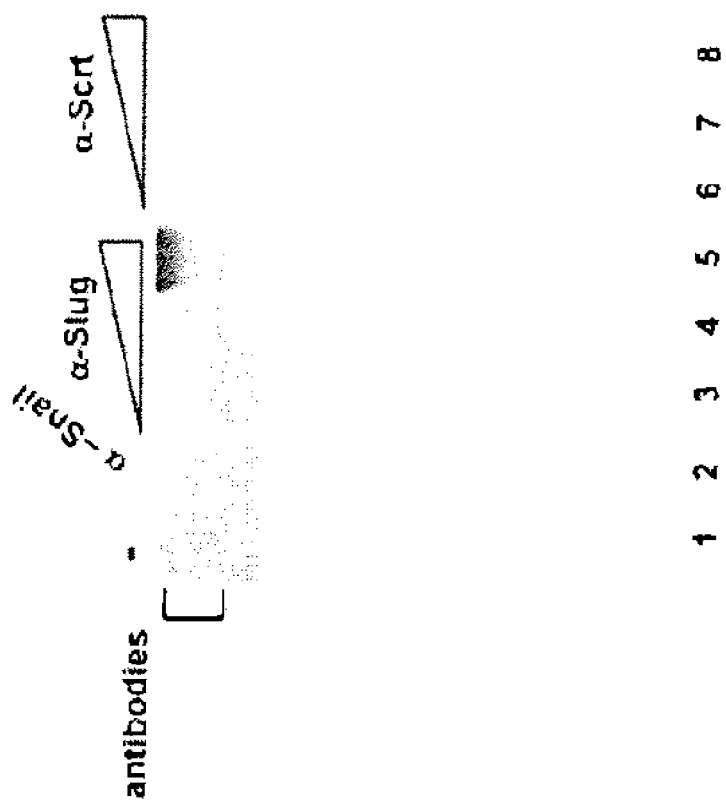
FIG. 5C is a gel showing the result of an EMSA as above using antibodies against Snail, Slug, and Scratch. hSlug and hScratch bind to the E2 box generated by the −3081(T) polymorphism of the hNET gene, but Snail does not.

A supershift EMSA was performed using antibodies against hδEF1/ZEB, hSnail, hScratch, and hSlug. Incubation of nucleic acid extracts with anti-hSlug and anti-hScratch, but not anti-hSnail retarded the migration of the major DNA-protein complex or diminished formation of that complex (FIGS. 5B and 5C). Thus, it is concluded that hSlug and hScratch transcriptional regulators have binding specificity for the E2-box created by the −3081(T) allele.

Figure 5D:
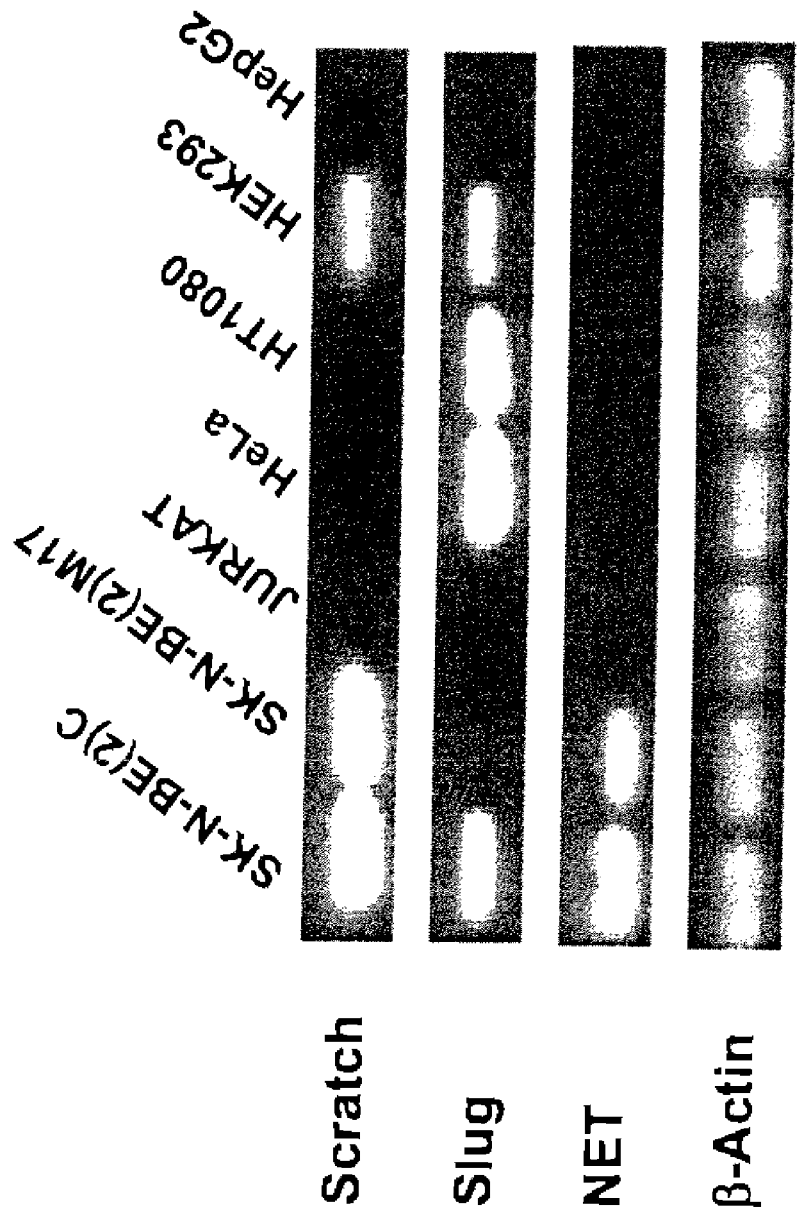
FIG. 5D is a gel showing the expression pattern of Slug, Scratch, and hNET expression in a variety of experimental cell lines.

Using RT-PCR, it was found that both Slug and Scratch were expressed in the NET-expressing cell lines. It was also found that hSlug and hScratch were expressed in some cell lines that did not express NET (FIG. 5D).

hslug and hScratch Decrease the hNET Promoter Activity in an Allele-Specific Manner SK-N-BE(2)C cells were used to investigate transcriptional regulation by the hNET promoter with hSlug and hScratch. The SK-N-BE(2)C cells were transfected with a luciferase reporter gene construct operably linked to a portion of the hNET promoter comprising either −3081(A) or −3081 (T). These constructs were designated pNET4000(i)LUC(A) or pNET4000(i)LUC(T), respectively. The cells were cotransfected with an expression vector comprising either Slug or Scratch. The luciferase activity was measured.

The luciferase plasmid pNET4000(i)LUC(A) was obtained by insertion of a Sal I and Xho I fragment of the plasmid pNET4000(i)CAT (14) into pGL3-Basic (Promega) digested with Xho I to yield pNET4000(i)LUC(A). The fragment between −−4000 and −3018 was amplified by PCR using the sense primer (5'-CATGGCAAGCTTGAAT TCAGGGCAGGTCAGCTG-3'; SEQ ID NO.:5) and the antisense primer (5'-GATACTAAGC TTGAGACAG-CAAAGGGA AGGAAACCA-3'; SEQ ID NO.: 6), digested with Hind III, and subcloned into pBLCAT2 or pNET133(i)

CAT (14) that had been cut with Hind III to yield pNET983 (A)TK-CAT. Constructs, pNET4000(i)LUC(T) and pNET983(T)TK-CAT, containing the T nucleotide at −3081 were generated by the Transformer Mutagenesis kit (Clonetech). Constructs with correct mutation were confirmed by restriction enzyme and sequencing analysis. Double-stranded DNAs containing −3092 to −3072 bp were generated by annealing the sense and antisense oligonucleotides containing either A or T nucleotide at the −3081 position, and self-ligated to generate multiple copies of A or T. The multimers were blunt-ended with Klenow (NE Biolabs) and inserted upstream of the TK promoter and luciferase gene (phRL-TK, Promega). An 807 bp coding fragment of hSlug and a 785 bp coding fragment of hSnail were produced by RT-PCR from SK-N-BE(2)C poly(A+) RNA. The PCR fragments were cloned into the pcDNA3.1 zeo(+) (Invitrogen) eukaryotic expression vector to produce pCMV-Slug and pCMV-Snail, respectively.

Figure 6A:
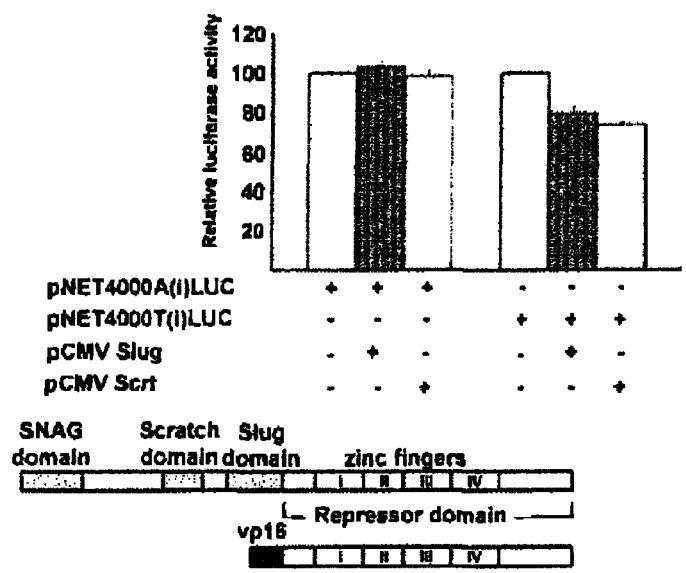
FIG. 6A is a bar graph showing the relative luciferase activity of SK-N-BE(2)C cells that were transiently cotransfected with reporter constructs having either a −3081(A) or −3081(T) hNET promoter and either hSlug or hScratch expression vectors. To compare the trans-repression directly, basal luciferase activity driven by each reporter construct was set to 100%.

Cotransfection of hSlug or hScratch had little effect on the reporter activity of the pNET4000(i)LUC(A) construct, but both hSlug and hScratch repressed the promoter activity of pNET4000(i)LUC(T). These hSnail family proteins are, therefore, capable of repressing the reporter gene activity in an allele-specific manner (FIG. 6A).

Next, the region N-terminal to the DNA-binding domain of hSlug and hScratch was replaced with the transactivation domain from herpes simplex virus VP16 to investigate whether hSlug and hScratch are responsible for repression observed in the pNET4000(i)LUC(T) constructs.

The VP16/Slug hybrid was constructed by replacing the N-terminal 118 amino acids of hSlug with the transactivation domain of VP16 protein. The integrity of all sequences for hSnail, hSlug and VP16/Slug cDNAs were verified by DNA sequence analysis.

Figure 6B:
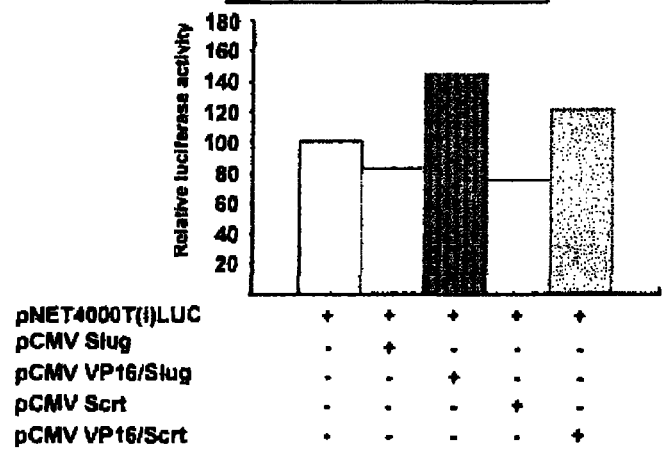
FIG. 6B is a bar graph showing the relative luciferase activity of cells co-transfected with either a −3081 (A) or −3081(T) allele of the 4.0 kb hNET promoter-luciferase reporter construct and an expression plasmid containing either a functional or a dominant negative hSlug construct or a functional or dominant negative hScratch construct. A schematic of the overall structure of Snail family proteins (including hSlug and hScratch) and the dominant negative constructs is provided. The activating form of Slug was constructed by replacing the N-terminal repressor domain with the activation domain of VP 16 (upper panel). Basal promoter activity driven by the 4.0 kb hNET promoter-luciferase reporter constructs containing an A allele at −3081 was set to 100%.

The luciferase activity driven by the pNET4000(i)LUC(T) construct was consistently reduced to 80% of that driven by pNET4000(i)LUC(A) construct. Cotransfection of the Slug expression vector with the pNET4000(i)LUC(T) construct further decreased the reporter gene activity. The reduction of promoter activity caused by the T-allele derived sequence was recovered by cotransfection with a VP 16/Slug expression vector, suggesting the direct involvement of the Slug protein in repression by T-allele derived sequences (FIG. 6B).

These results demonstrate that hSlug protein binds to the E2 box element created by the −3081(T) polymorphism and results in decreased transcriptional activity of NET gene expression inside cells.

Pharmacogenomic Approaches to hNET Therapy

A patient's status with regard to the −3081(A/T) hNET polymorphism of the present invention may be predictive of their response to hNET inhibitor therapy. As discussed above, the −3081(T) allele results in reduced hNET gene expression and protein levels. Thus, the efficacy of hNET inhibitor therapy is reduced in patients carrying this polymorphism compared to patients having the wildtype −3081(A) allele.

Thus, knowledge of a patient's status with respect to this polymorphism may guide the attending physician in the selection of appropriate therapeutics, including hNET inhibitors, and/or may guide the appropriate dosing of such inhibitors. Specifically, hNET-based therapies that may be guided by this information include, for example, selective hNET inhibitors such as atomoxetine and reboxetine, as well as mixed hNET and serotonin reuptake inhibitors such as clovoxamine, duloxetine, nefazonone, sibutramine, and venlafaxine (15). The former class of therapeutics are used to treat attentional disorders (e.g., ADHD), depression, narco- lepsy, panic disorder, schizophrenia, and bulimia. The latter class of therapeutics additionally are used to treat depression and neuropathic pain.

Enhancing hNET Promoter Activity to Treat ADHD

The symptoms of ADHD, particularly iADHD, may be ameliorated by enhancing hNET promoter activity in patients carrying the −3081(T) allele as described herein. One therapeutic strategy is to reduce the binding and/or efficacy of transcriptional repressors such as the Snail-family proteins (e.g., hSlug and hScratch).

Transcriptional repressors of the Snail superfamily are composed of a highly conserved C-terminal region containing 4-6 zinc fingers of the $C_2H_2$ type and these zinc fingers mediate sequence-specific interactions with DNA. hSlug is involved in the mesoderm and neural crest formation, as well as in the progression of epithelial tumors, while Scratch promotes neuronal differentiation (17, 41). Slug recruits a co-repressor, CtBP-1, that in turn recruits HDAC and leads to gene repression (20). Thus, ADHD patients having the −3081 (T) allele are treated by inhibiting any one the following interactions: Slug with the E2 box motif created by the −3081 (T) polymorphism; hSlug with CtBP-1; and CtBP-1 with HDAC.

A dominant negative Snail superfamily protein (e.g., hSlug or hScratch protein) is administered to the ADHD patient. The dominant negative protein may contain mutations in one or more the zinc finger domains or other region of the protein that destroys DNA binding activity. A dominant negative hSlug protein may contain mutations that prevent it from binding to the CtBP-1 protein. Mutated Snail superfamily proteins may be administered as soluble proteins or fragments, encapsulated in liposomes or other delivery vehicles, or administered using RNA interference (RNAi), siRNA, or gene therapy techniques such as those described below.

RNA Interference

RNAi is a method for decreasing the cellular expression of specific proteins of interest (32). In RNAi, gene silencing is typically triggered post-transcriptionally by the presence of double-stranded RNA (dsRNA) in a cell. This dsRNA is processed intracellularly into shorter pieces called small interfering RNAs (siRNAs). The introduction of siRNAs into cells either by transfection of dsRNAs or through expression of siRNAs using a plasmid-based expression system is increasingly being used to create loss-of-function phenotypes in mammalian cells. Based on the nucleotide sequence of the Snail superfamily genes (e.g., the hSlug or hScratch genes), various RNAi molecules may be designed to inhibit the expression of Snail superfamily genes in vivo.

Double-stranded RNA (dsRNA) molecules contain distinct strands of RNA that have formed a complex, or a single RNA strand that has formed a duplex (small hairpin (sh) RNA).

Typically, dsRNAs are about 21 or 22 base pairs, but may be shorter or longer if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are well known in the art (33).

Small hairpin RNAs consist of a stem-loop structure with optional 3' UU-overhangs. While there may be variation, stems can range from 21 to 31 base pairs (desirably 25 to 29 bp), and the loops can range from 4 to 30 base pairs (desirably 4 to 23 base pairs). For expression of shRNAs within cells, plasmid vectors containing, for example, either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short (e.g., about 21-25 nucleotide) double stranded RNAs are effective at down-regulating gene expression in vitro (mammalian tissue culture cell lines) and in vivo (34).

Methods for producing siRNAs are standard in the art. For example, the siRNA can be chemically synthesized or recombinantly produced. For example, short sense and antisense RNA oligomers can be synthesized and annealed to form double-stranded RNA structures with 2-nucleotide overhangs at each end (35). These double-stranded siRNA structures can then be directly introduced to cells, either by passive uptake or a delivery system of choice, such as described below. In some embodiments, siRNAs are generated by processing longer double-stranded RNAs, for example, in the presence of the enzyme dicer under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In particular embodiments, at least one strand of the siRNA molecules has a 3' overhang from about 1 to about 6 nucleotides in length, though it may be from 2 to 4 nucleotides in length. More particularly, the 3' overhangs are 1-3 nucleotides in length. In other embodiments, one strand has a 3' overhang and the other strand is blunt-ended or also has an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In some embodiments, the RNAi construct is in the form of a hairpin structure. The hairpin RNAs is synthesized exogenously or is formed by transcribing from RNA polymerase III promoters in vivo. Examples of making and using such hairpin RNAs for gene silencing in mammalian cells are described in the art (36). Preferably, hairpin RNAs are engineered in cells or in animals to ensure continuous and stable suppression of a desired gene. It is known in the art that siRNAs are produced by processing a hairpin RNA in the cell.

In other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences are the same sequence, e.g., flanked by inverted promoters, or are two separate sequences each under transcriptional control of separate promoters. After the coding sequence is transcribed, the complementary RNA transcripts base-pair to form the double-stranded RNA. PCT application WO01/77350 describes an exemplary vector for bi-directional transcription of a transgene to yield both sense and antisense RNA transcripts of the same transgene in a eukaryotic cell.

Gene Therapy

Gene therapy is another therapeutic approach for inhibiting the activity Snail superfamily genes/proteins (e.g., hSlug and hScratch) in a patient. Heterologous nucleic acid molecules, encoding for example an anti-sense nucleic acid or a dominant negative protein, is delivered to the target cell of interest. The nucleic acid molecules are delivered to those cells in a form in which they can be taken up by the cells and so that sufficient levels of the nucleic acid or protein can be produced to provide a therapeutic benefit. Alternatively, gene therapy may be used to deliver a nucleic acid encoding a wild-type hNET gene to the target cells in order to increase the level of hNET protein. Methods and compositions for use in gene therapy are well known in the art (42).

Transducing viral (e.g., retroviral, adenoviral, and adeno-associated viral) vectors are used for somatic cell gene therapy, especially because of their high efficiency of infection and stable integration and expression (37).

Adenoviruses are able to transfect a wide variety of cell types, including non-dividing cells. There are more than 50 serotypes of adenoviruses that are known in the art, but the most commonly used serotypes for gene therapy are type 2 and type 5. Typically, these viruses are replication-defective; genetically modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (43).

Retroviruses are also useful as gene therapy vectors and usually are not capable of transfecting non-dividing cells. The invention includes use of any appropriate type of retrovirus that is known in the art, including, but not limited to, lentivirus, HIV, SIV, FIV, EIAV, and Moloney Murine Leukemia Virus (MoMLV). Typically, therapeutically useful retroviruses including deletions of the gag, pol, or env genes (38, 39).

Adeno-associated virus (AAV) vectors can achieve latent infection of a broad range of cell types, exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (44).

Herpes simplex virus (HSV) replicates in epithelial cells, but is able to stay in a latent state in non-dividing cells such as the midbrain dopaminergic neurons. The gene of interest may be inserted into the LAT region of HSV, which is expressed during latency. Other viruses that have been shown to be useful in gene therapy include parainfluenza viruses, poxviruses, and alphaviruses, including Semliki forest virus, Sinbis virus, and Venezuelan equine encephalitis virus (45).

Non-viral approaches may be employed for the introduction of therapeutic nucleic acids to target cells of a patient. For example, a nucleic acid molecule can be introduced into a cell by administering the nucleic acid in the presence of lipofection or by asialoorosomucoid-polylysine conjugation (40). Other exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation (46).

Gene transfer also may be achieved using non-viral means involving transfection in vitro. Such methods include the use of calcium phosphate, DEAE dextran, electroporation, and protoplast fusion. Exemplary cationic liposomes for use in this invention are DOTMA, DOPE, DOSPA, DOTAP, DC-Chol, Lipid GL-67™., and EDMPC (47). These liposomes may be used in vivo or ex vivo to encapsulate a G-substrate vector for delivery into target cells. Liposomes are believed to be beneficial for delivery of DNA into a cell. Transplantation of normal genes into the affected tissues of a patient is accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in gene therapy methods may be directed from any suitable promoter and regulated by any appropriate mammalian regulatory element. Typically, vectors made in accordance with the principles of this disclosure will contain promoters that will cause constitutive expression of the coding sequence. Desirably, neuron-specific promoters are used in order to limit or eliminate ectopic expression in the event that the vector is incorporated into cells outside of the target region. Several regulatory elements are well known in the art to direct neuronal specific gene expression including, for example, the neural-specific enolase (NSE), and synapsin-1 promoters (48). Alternatively, if a genomic clone is used as a therapeutic construct, regulation is mediated by the cognate regulatory sequences or, if desired, by regulatory sequences derived from a heterologous source, including any of the promoters or regulatory elements described above.

Another therapeutic approach included in the invention involves administration of a recombinant nuclear encoded mitochondrial metabolism or proteasomal polypeptide, either directly to the site of a potential or actual disease-affected tissue (for example, by injection into the ventricles of the brain or into the cerebrospinal fluid) or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions. Generally, between 0.1 mg and 100 mg, is administered per day to an adult in any pharmaceutically acceptable formulation.

Identification of Candidate Compounds for Treatment of ADHD

A candidate compound that is beneficial in the treatment of ADHD is identified using the methods and compositions of the present invention. A candidate compound is identified for its ability to increase the transcription of the hNET gene, translation of the hNET RNA, or reduced the binding (or other biological activity) of a Snail superfamily protein (e.g., hSlug or hScratch) to the E2 box in the hNET promoter.

One method for evaluating the ability of a candidate compound to increase hNET gene translation is by measuring the binding between the Snail superfamily protein and the E2 box motif created by the −3081(T) polymorphism. Compounds that reduce this binding are useful for the treatment of attentional disorders. Such screening methods are performed in cell-based or cell-free assay systems and typically will measure, directly or indirectly, the DNA binding event.

Another method for evaluating the ability of candidate compounds to increase hNET gene translation, in a cell-based assay, is to provide cells that express Slug and the hNET gene under the control of a promoter having the −3081(T) polymorphism, and contact that cell with a candidate compound. Compounds that increase the level hNET expression are useful for treating attentional disorders. Alternatively, the hNET coding sequence may be replaced with any convenient reporter gene (e.g., luciferase, β-galactosidase, etc.) and the product of that reporter gene measured as an index of promoter function.

Any number of methods are available for carrying out screening assays to identify new candidate compounds that promote the expression of an hNET gene or inhibit the expression of a Snail superfamily gene. In one working example, candidate compounds are added at varying concentrations to the culture medium of cultured cells expressing one of the desired nucleic acid sequences. Gene expression is then measured, for example, by microarray analysis, Northern blot analysis, or RT-PCR, using any appropriate fragment prepared from the nucleic acid molecule as a hybridization probe. The level of gene expression in the presence of the candidate compound is compared to the level measured in a control culture medium lacking the candidate compound. A compound which promotes a change (increase of hNET or decrease of Slug or Scratch) in the expression of a gene is useful in the invention and is used as a therapeutic to treat a human patient with the −3081(T) allele.

In another working example, the effect of candidate compounds is measured at the level of hNET or Snail superfamily protein (e.g., hSlug or hScratch) production using the same general approach and standard immunological techniques, such as Western blotting or immunoprecipitation with an antibody specific for either protein. For example, immunoassays are used to detect or monitor the expression of at least one of the polypeptides of the invention in an organism. Polyclonal or monoclonal antibodies that are capable of binding to an hNET an hSlug, or an hScratch protein may be used in any standard immunoassay format (e.g., ELISA, Western blot, or RIA assay) to measure the level of the protein.

Pharmaceutical Compositions for ADHD Therapeutics

The present invention includes the administration of compounds for the treatment of ADHD. Peptide agents of the invention, such as dominant negative Slug, can be administered to a subject, e.g., a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline.

Other physiologically acceptable carriers and their formulations are known to one skilled in the art and described, for example, in Remington: The Science and Practice of Pharmacy, (21st edition), ed. R. Hendrickson, 2005, Lippincott Williams & Wilkins, New York, N.Y.

Pharmaceutical formulations of a therapeutically effective amount of a peptide agent or candidate compound of the invention, or pharmaceutically acceptable salt-thereof, can be administered orally, parenterally (e.g. intramuscular, intraperitoneal, intravenous, or subcutaneous injection), or by intrathecal or intracerebroventricular injection in an admixture with a pharmaceutically acceptable carrier adapted for the route of administration.

Methods known in the art for making formulations are found, for example, in Remington: The Science and Practice of Pharmacy, (21st edition), ed. R. Hendrickson, 2005, Lippincott Williams & Wilkins, New York, N.Y. Compositions intended for oral use are prepared in solid or liquid forms according to any method known to the art for the manufacture of pharmaceutical compositions. The compositions optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The amount of active ingredient in the compositions of the invention is varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 µg/kg to 100 mg/kg of body weight are administered daily as a single dose or divided into multiple doses. Desirably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The protein or therapeutic compound of the invention may be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

The protein or therapeutic compound of the present invention can be prepared in any suitable manner. The protein or therapeutic compound can be isolated from naturally occurring 110 sources, recombinantly produced, or produced synthetically, or produced by a combination of these methods. The synthesis of short peptides is well known in the art. See e.g. Stewart et al., Solid Phase Peptide Synthesis (Pierce Chemical Co., 2d ed., 1984).

REFERENCES

1. Iversen, (1963) *Br J Pharmacol Chemother* 21, 523-37.
2. Xu, et al. (2000) *Nat Neurosci* 3, 465-71.
3. Amara, et al. (1993) *Annu Rev Neurosci* 16, 73-93.
4. Bruss, et al. (1993) *Hum Genet* 91, 278-80.
5. Pacholczyk, et al. (1991) *Nature* 350, 350-4.
6. Klimek, et al. (1997) *J Neurosci* 17, 8451-8.
7. Heim, et al. (2001) *Biol Psychiatry* 49, 1023-39.
8. Biederman, et al. (2002) *Pediatrics* 110, e75.
9. American Psychiatric Association. (1994) Diagnostic and Statistical Manual of Mental Disorders, 4th edn. Washington D.C.
10. Hahn, et al. (2005) *Mol Pharmacol* 68, 457-66.
11. Hahn, et al. (2003) *J Neurosci* 23, 4470-8.
12. Shannon, et al. (2000) *N Engl J Med* 342, 541-9.
13. Urwin, et al. (2002) *Mol Psychiatry* 7, 652-7.
14. Kim, et al. (1998) *Nucleic Acids Res* 26, 362-7.
15. Iversen (2000) Mol. Psychiatry 5, 357-362.
16. Funahashi, et al. (1993) *Development* 119, 433-46.
17. Nieto (2002) *Nat Rev Mol Cell Biol* 3, 155-66.
18. Stober, et al. (1999) *Am J Med Genet* 88, 158-63.
19. Bobb, et al. (2005) *Am J Med Genet B Neuropsychiatr Genet* 134, 67-72.
20. Kang, et al. (2004) *Cell* 118, 277-9.
21. Barkley, R. A. (1997) *J Dev Behav Pediatr* 18, 271-9.
22. Todd, R et al. (2001) *Biol Psychiatry* 50, 151-8.
23. Solanto, M. V. (1998) *Behav Brain Res* 94, 127-52.
24. Biederman, et al. (2000) *J Am Acad Child Adolesc Psychiatry* 39, 1330-3.
25. Malone, et al. (1994) *J Child Neurol* 9, 181-9.
26. Dougherty, et al. (1999) *Lancet* 354, 2132-3.
27. Nigg, et al. (2002) *J Am Acad Child Adolesc Psychiatry* 41, 59-66.

28. Trommer, et al. (1988) *Ann Neurol* 24, 610-4.
29. Posner, et al. (1990) *Annu Rev Neurosci* 13, 25-42.
30. Kaufman, et al. (1997) *J Am Acad Child Adolesc Psychiatry* 36, 980-8.
31. Ambrosini, (2000) *J Am Acad Child Adolesc Psychiatry* 39, 49-58.
32. Tuschl (2001) *Chembiochem* 2, 239-245; Sharp (2000) *Genes & Devel.* 15, 485-490; Hutvagner et al. (2002) *Curr. Opin. Genet. Devel.* 12: 225-232; Hannon (2002) *Nature* 418, 244-251.
33. Brummelkamp et al. (2002) *Science* 296, 550-553; Paddison et al. (2002) *Genes & Devel.* 16, 948-958; Paul et al. (2002) *Nature Biotechnol.* 20, 505-508; Sui et al. (2002) *Proc. Natl. Acad. Sci. USA* 99, 5515-5520; Yu et al. (2002) *Proc. Natl. Acad. Sci. USA* 99, 6047-6052; Miyagishi et al. (2002) *Nature Biotechnol.* 20:497-500; Lee et al. (2002) *Nature Biotechnol.* 20, 500-505.
34. Elbashir et al. (2001) *Nature* 411, 494-498; McCaffrey et al. (2002) *Nature* 418, 38-9; McCaffrey et al. (2003) *Hepatology* 38, 503-8; Sang et al. (2003) Nature Medicine 9, 347-351; U.S. Patent Publications 2003/0153519, 2003/0157030, 2003/0170891, and 2003/0180756.
35. Caplen, et al. (2001) *Proc. Natl. Acad. Sci, USA* 98, 9742-9747; Elbashir, et al. *EMBO J.* (2001) 20, 6877-88.
36. Paddison et al. (2002) *Genes Dev.* 16, 948-58; McCaffrey et al. (2002) *Nature* 418, 38-9; McManus et al. (2002) *RNA* 8, 842-50; Yu et al. (2002) *Proc Natl. Acad. Sci. USA* 99, 6047-52.
37. Cayouette et al. (1997) *Human Gene Therapy* 8, 423-430; Kido et al. (1996) *Current Eye Research* 15, 833-844; Bloomer et al. (1997) *J. Virology* 71, 6641-6649; Naldini et al. (1996) *Science* 272, 263-267; Miyoshi et al. (1997) *Proc. Natl. Acad. Sci. USA* 94, 10319.
38. Miller (1990) *Human Gene Therapy* 15, 14; Friedman, (1989) *Science* 244, 1275-1281; Eglitis et al. (1988) *BioTechniques* 6:608-614; Tolstoshev et al. (1990) *Curr. Opin. Biotechnol.* 1:55-61; Sharp (1991) *Lancet* 337:1277-1278; Cornetta et al. (1987) *Nuc. Acid Res. Mol. Biol.* 36, 311-322; Anderson (1984) *Science* 226, 401-409; Moen (1991) *Blood Cells* 17, 407-416; Miller et al. (1989) *Biotechnology* 7, 980-990; Le Gal La Salle et al. (1993) *Science* 259, 988-990; Johnson (1995) *Chest* 107:77S-83S.
39. Rosenberg et al. (1990) *N. Engl. J. Med.* 323, 370; U.S. Pat. No. 5,399,346.
40. Felgner et al. (1987) *Proc. Natl. Acad. Sci. USA* 84, 7413; Ono et al. (1990) *Neurosci. Lett.* 17, 259; Brigham et al. (1989) *Am. J. Med. Sci.* 298, 278; Staubinger et al. (1983) *Meth. Enzymol.* 101, 512; Wu et al. (1988) *J. Biol. Chem.* 263, 14621; Wu et al. (1989) *J. Biol. Chem.* 264, 16985.
41. Przybylska et al. (2004) J. Gene Med., 6: 85-92; Svahn, et al. (2004) J. Gene Med., 6: S36-S44.
42. Morelli et al. (1999) J. Gen. Virol. 80, 571-583.
43. Cubells et al. (1997) Am. J. Med. Genet. 74, 374-379.
44. International HapMap Contortium (2005) Nature 437, 1299-1320. 1465-1468; Zhu, et al. (1993) Science, 261: 209-211; Nabel, et al. (1989) Science, 244:1342-1344.
47. Przybylska et al. (2004) J. Gene Med., 6: 85-92; Svahn, et al. (2004) J. Gene Med., 6: S36-S44.
48. Morelli et al. (1999) J. Gen. Virol. 80, 571-583.
49. Cubells et al. (1997) Am. J. Med. Genet. 74, 374-379.
50. International HapMap Consortium (2005) Nature 437, 1299-1320.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for diagnosing a subject as having an increased likelihood of developing attention deficit hyperactivity disorder (ADHD), comprising the steps of:
   (a) determining the nucleotide base in the human norepinephrine transporter (hNET) gene promoter corresponding to position 954 of SEQ ID NO: 2; and
   (b) diagnosing the subject as having an increased likelihood of developing ADHD when said nucleotide is thymine.

2. The method of claim 1, wherein said method comprises at least one method selected from the group consisting of restriction fragment length polymorphism analysis, polymerase chain reaction, nucleotide sequencing, nucleotide sequencing by primer extension, and allele-specific polymerase chain reaction.

3. The method of claim 2, wherein said method comprises restriction fragment length polymorphism analysis.

4. The method of claim 3, wherein said restriction fragment length polymorphism analysis is performed using endonuclease BsrI.

5. A method for confirming a diagnosis of attention deficit hyperactivity disorder (ADHD) in a subject, comprising the steps of:
   (a) determining the nucleotide base in the human norepinephrine transporter (hNET) gene promoter corresponding to position 954 of SEQ ID NO: 2; and
   (b) confirming the diagnosis of ADHD in the subject when said nucleotide is thymine.

6. The method of claim 5, wherein said method comprises at least one method selected from the group consisting of restriction fragment length polymorphism analysis, polymerase chain reaction, nucleotide sequencing, nucleotide sequencing by primer extension, and allele-specific polymerase chain reaction.

7. The method of claim 6, wherein said method comprises restriction fragment length polymorphism analysis.

8. The method of claim 7, wherein said restriction fragment length polymorphism analysis is performed using endonuclease BsrI.

\* \* \* \* \*

UNITED STATES PATENT AND TRADEMARK OFFICE
CERTIFICATE OF CORRECTION

PATENT NO. : 7,807,362 B2
APPLICATION NO. : 11/674817
DATED : October 5, 2010
INVENTOR(S) : Kwang-Soo Kim and Chun-Hyung Kim It is certified that error appears in the above-identified patent and that said Letters Patent is hereby corrected as shown below:

IN THE SPECIFICATION

Column 9, line 12, "method (49) in the full", should read --method (43) in full--;

Column 9, line 30, "database (50) revealed", should read --database (44) revealed--;

Column 14, line 18, "differentiation (17, 41) Slug", should read --differentiation (17) Slug--;

Column 16, line 23, "known in the art (42)", should read --known in the art.--;

Column 16, line 37, "packaging signal (43).", should read --packaging signal.--;

Column 16, lines 51-52, "and AAV6 (44).", should read --and AAV6.--;

Column 16, line 60, "encephalitis virus (45).", should read --encephalitis virus.--;

Column 17, line 10, "electroporation (46).", should read --electroporation.--;

Column 17, line 16, "EDMPC (47). These", should read --EDMPC (41). These--; and

Column 17, line 37, "promoters (48). Alternatively,", should read --promoters (42). Alternatively,--.

Signed and Sealed this
Seventeenth Day of April, 2012

David J. Kappos
*Director of the United States Patent and Trademark Office*

SEQUENCE LISTING

```
<160> NUMBER OF SEQ ID NOS: 10

<210> SEQ ID NO 1
<211> LENGTH: 1017
<212> TYPE: DNA
<213> ORGANISM: Homo sapiens

<400> SEQUENCE: 1
gaattcaggg caggtcagct gcagtgtaat atatgcctat tgtcccctga tcaagacaga      60
aagacagaat gaaaaggaag aaggaaggaa ggaacggagg aaagaaaaga gggatggagg     120
aaacaaatat gtaggcaaac ctctcctcct ttttttcctt agtctcctca ttggtgccat     180
ggaggtgtag gttctgatag cgtcctcagc ggacacaggc ccttggattc taaatgtgtc     240
ccagcccagc tgttgtgtgt cagggcccca gtgtctgtgg ggagatggcc agagatggac     300
tcacagcatc agccattgcc ttttacccca tggcctgtgt caccaagtgc catggtaagt     360
ggaagtgatg gctccccaga gatcacatta gctctgataa tgctccagcc tcccatgcac     420
aacttgccct caggccacct ggctgggcag gaagaagggc tcccagagaa gccacatggc     480
cccatggcgg tgagtctggg cgagagatgg agagagacgc cttcccttt agcccagtcc     540
```

-continued

```
cagcctagtg tcctcactgc tgaccccogg tagtctctga aaccacagat ggagctccca      600
gacttgctga ttggcccocg tgatggcgtg cgcattagga ggaaatgcct ccctccaccc      660
ttgtagcaaa cacttccagc tccatgccca cccccttat catccactgt tcctgccagt       720
gcagacccaa cccaatggct tcgtgctgcc agtacctggg gctctgctgt tagccttttct    780 ctggcagcag gacaggctca tccctcttat cagacaggct ggacttggtg ggaagttgac      840
actctggggg cggccttcat ggataaatac tgtagttttc ttgcccctca agtgagacaa      900
ccccaaggcg tgctctgtgc agtctcccga ggcccccacc agggctgagc accagtttcc      960
ccagcagcaa gtgctcctta atctactttc tcctggtttc cttcccttttg ctgtctc      1017
```

<210> SEQ ID NO 2
<211> LENGTH: 1017
<212> TYPE: DNA
<213> ORGANISM: Homo sapiens

<400> SEQUENCE: 2

```
gaattcaggg caggtcagct gcagtgtaat atatgcctat tgtcccctga tcaagacaga      60
aagacagaat gaaaaggaag aaggaaggaa ggaacggagg aaagaaaaga gggatggagg      120
aaacaaatat gtaggcaaac ctctcctcct ttttttcctt agtctcctca ttggtgccat      180
ggaggtgtag gttctgatag cgtcctcagc ggacacaggc ccttggattc taaatgtgtc      240
ccagcccagc tgttgtgtgt cagggcccca gtgtctgtgg ggagatggcc agagatggac      300
tcacagcatc agccattgcc ttttacccca tggcctgtgt caccaagtgc catggtaagt      360
ggaagtgatg gctccccaga gatcacatta gctctgataa tgctccagcc tccatgcac     420 aacttgccct caggccacct ggctgggcag gaagaagggc tcccagagaa gccacatggc      480
cccatggcgg tgagtctggg cgagagatgg agagagacgc cttccctttt agcccagtcc      540
cagcctagtg tcctcactgc tgaccccocgg tagtctctga aaccacagat ggagctccca     600
gacttgctga ttggcccocg tgatggcgtg cgcattagga ggaaatgcct ccctccaccc      660
ttgtagcaaa cacttccagc tccatgccca cccccttat catccactgt tcctgccagt       720
gcagacccaa cccaatggct tcgtgctgcc agtacctggg gctctgctgt tagccttttct    780 ctggcagcag gacaggctca tccctcttat cagacaggct ggacttggtg ggaagttgac      840
actctggggg cggccttcat ggataaatac tgtagttttc ttgcccctca agtgagacaa      900
ccccaaggcg tgctctgtgc agtctcccga ggcccccacc agggctgagc acctgtttcc      960
ccagcagcaa gtgctcctta atctactttc tcctggtttc cttcccttttg ctgtctc      1017
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
ctgtagtttt cttgcccctc aag                                              23
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 4
ggctgagcac cwgtttccca                                              20

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catggcaagc ttgaattcag ggcaggtcag ctg                               33

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatactaagc ttgagacagc aaagggaagg aaacca                            36

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acccctttga ccacgagtc                                               19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acccctttgt ccacgagtc                                               19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggctgagcac cagtttcccc a                                            21

<210> SEQ ID NO 10
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 10
ggctgagcac ctgtttcccc a                                            21
```